United States Patent [19]
Fischell et al.

[11] Patent Number: 5,792,144
[45] Date of Patent: Aug. 11, 1998

[54] STENT DELIVERY CATHETER SYSTEM

[75] Inventors: Robert E. Fischell, Dayton, Md.;
David R. Fischell, Fair Haven, N.J.;
Tim A. Fischell, Richland, Mich.

[73] Assignee: Cathco, Inc., Dayton, Md.

[21] Appl. No.: 828,662

[22] Filed: Mar. 31, 1997

[51] Int. Cl.⁶ ................................................. A61M 29/00
[52] U.S. Cl. ................................................ 606/108; 606/194
[58] Field of Search ............................... 606/108, 194, 606/198, 192, 195; 623/1, 12

[56] References Cited

U.S. PATENT DOCUMENTS

| | | | |
|---|---|---|---|
| 4,768,507 | 9/1988 | Fischell et al. | 128/303 R |
| 4,969,890 | 11/1990 | Sugita et al. | 606/192 |
| 5,192,297 | 3/1993 | Hull | 606/195 |
| 5,344,426 | 9/1994 | Lau et al. | 606/198 |
| 5,639,274 | 6/1997 | Fischell et al. | |

FOREIGN PATENT DOCUMENTS 2102019  10/1992  Canada.
2111496  12/1992  Canada.

*Primary Examiner*—Michael Buiz
*Assistant Examiner*—Kevin Truong

[57] ABSTRACT

The present invention is a stent delivery catheter system for placing a stent within a stenosis in a vessel of a human body. The stent delivery catheter system utilizes a slideable sheath with a thin-walled distal portion that is situated coaxially over a stent that is placed onto a balloon located at the distal portion of a balloon angioplasty catheter. The distal end of a central portion of the sheath has an interior shoulder which is capable of exerting a distally directed push force on the balloon angioplasty catheter at a point that is just proximal to the stent. This push force is then transferred through the non-deployed stent to a gradually tapered, highly flexible, lubricity coated distal tip of the balloon angioplasty catheter. The structure of a continuous outer surface extending backward from the distal tip and onto the distal section of the sheath, plus the lubricity coating of the outer surfaces of the distal tip and the sheath, plus the increased stent delivery catheter system pushability provided by the sheath and the stent itself makes it possible for the stent delivery catheter system to be pushed through even very tight stenoses.

15 Claims, 5 Drawing Sheets

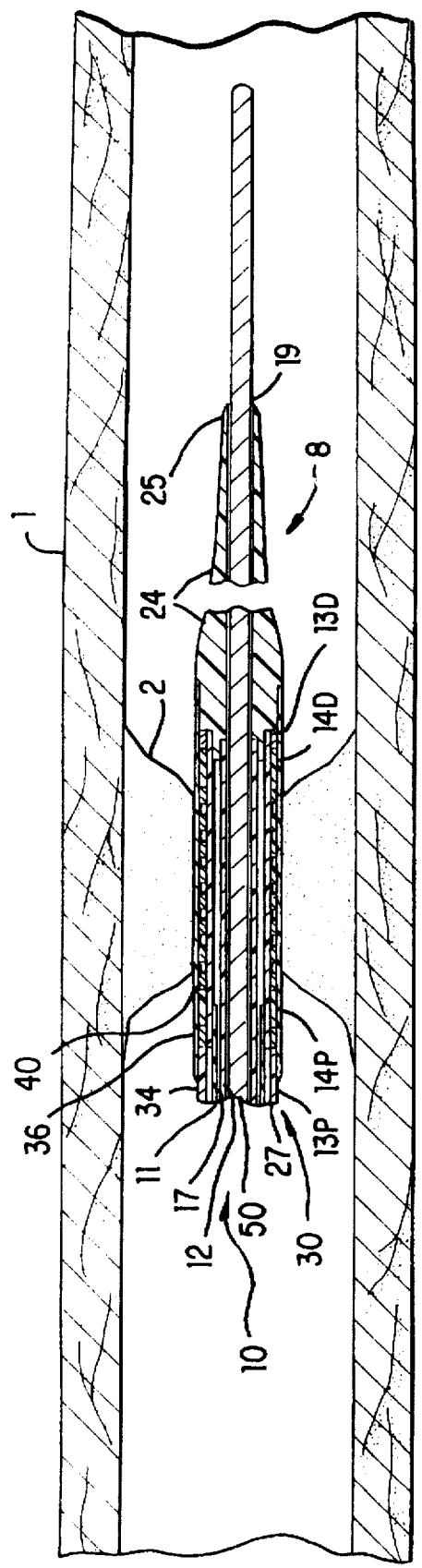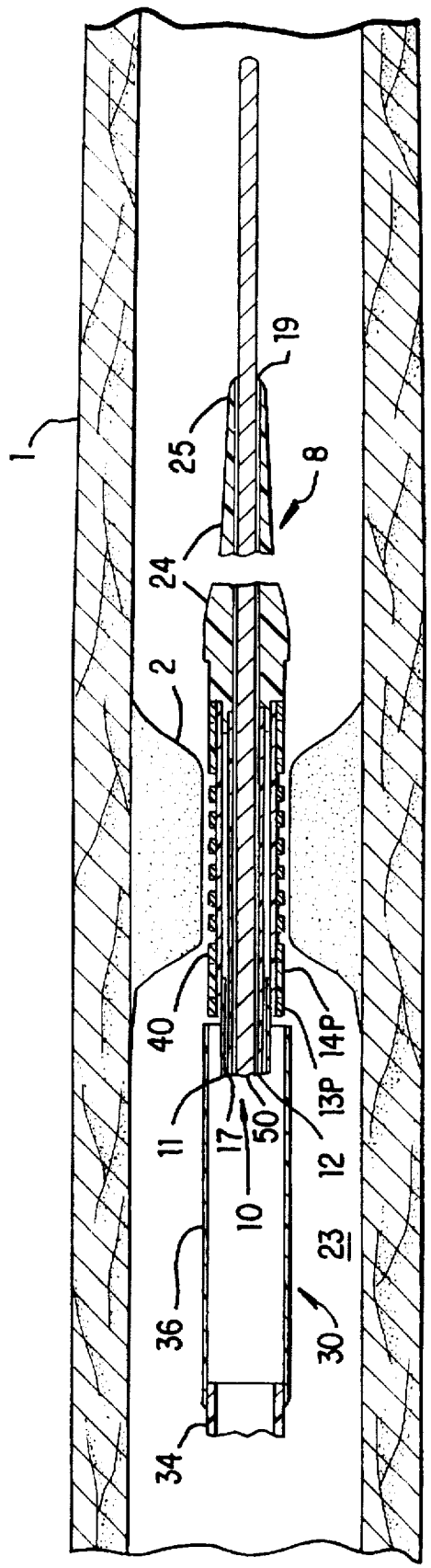

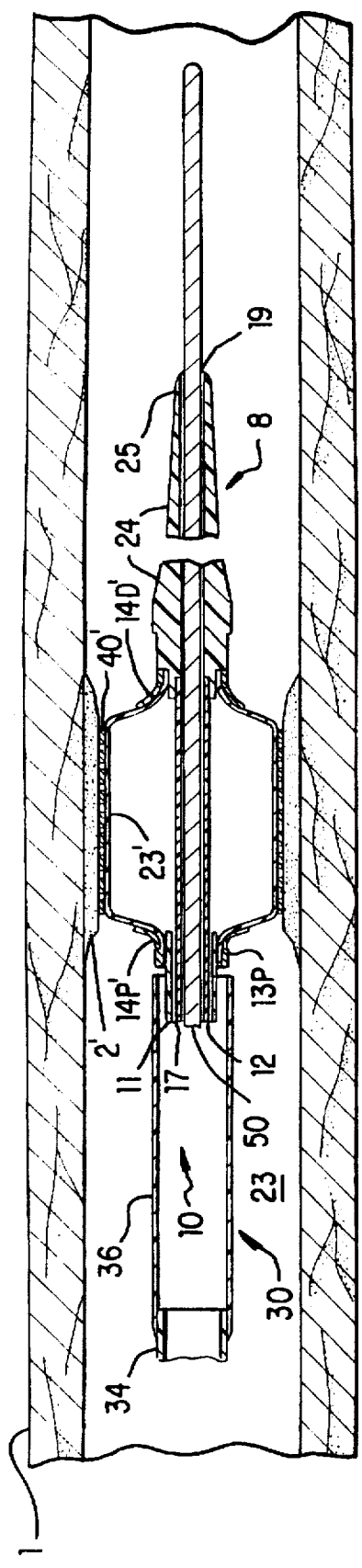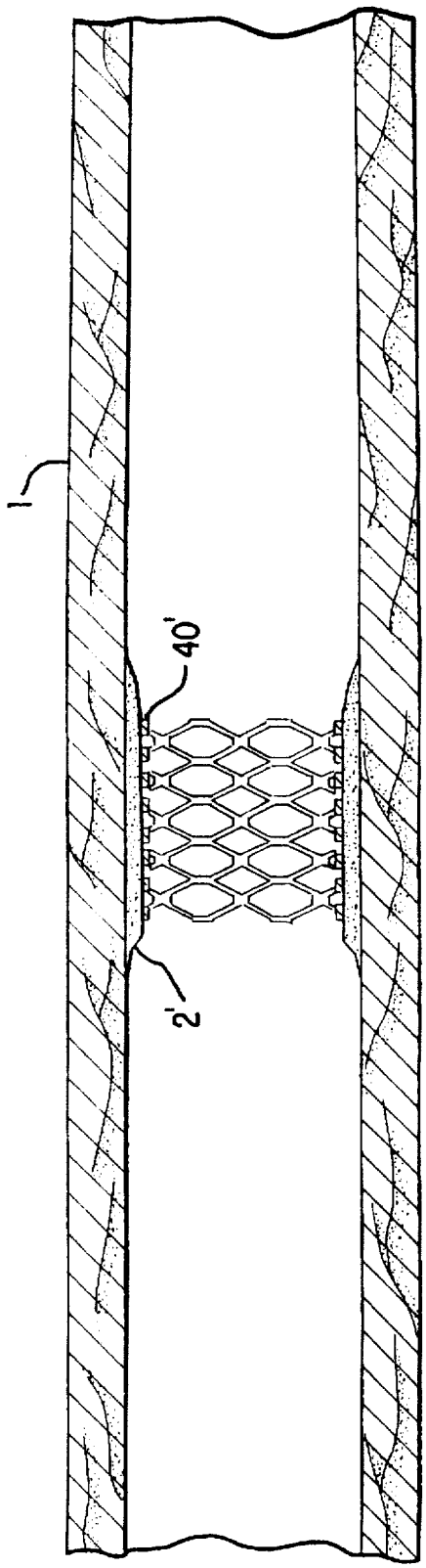

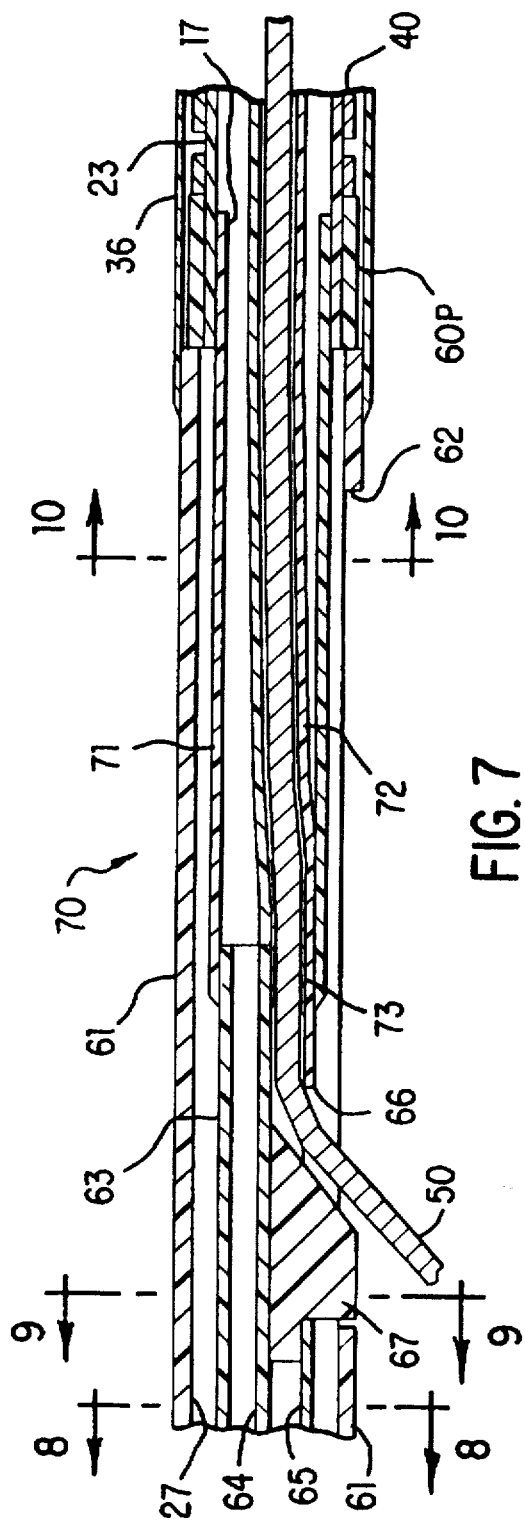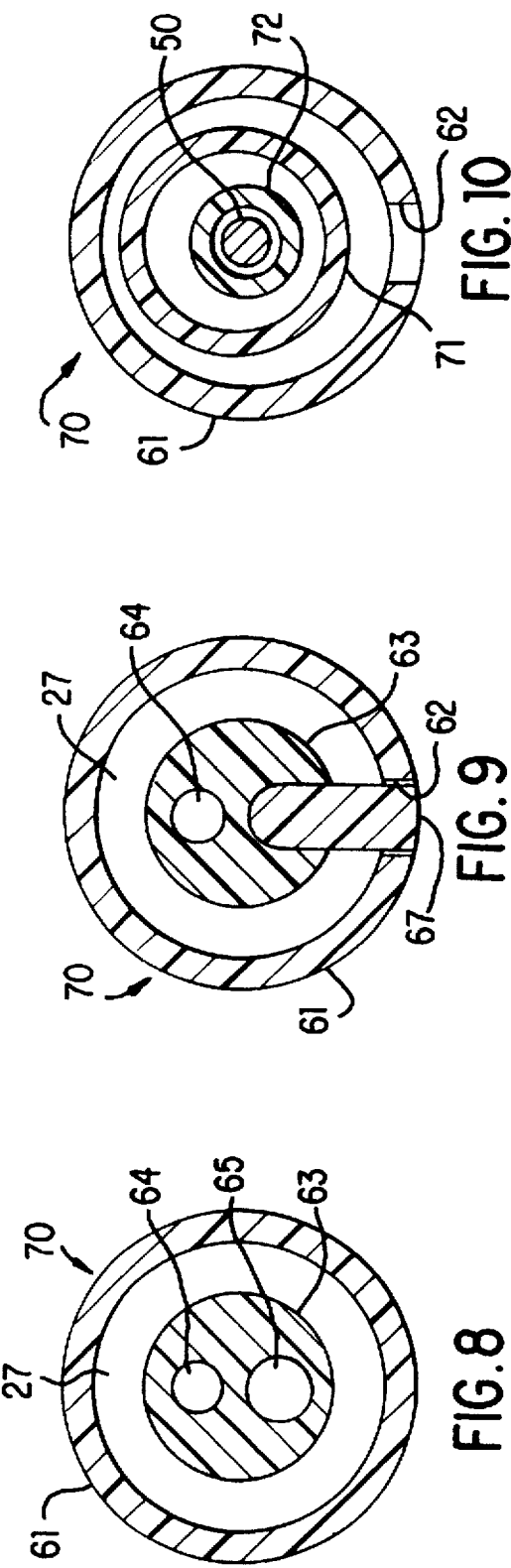

STENT DELIVERY CATHETER SYSTEM

FIELD OF USE

This invention is in the field of catheters to place stents into a stenosis in a vessel of a human body.

BACKGROUND OF THE INVENTION

Intravascular stents are well known in the field of interventional cardiology for the treatment of arterial stenoses. When placed through the body's vascular system, most stents are mounted onto a balloon angioplasty catheter with or without a cylindrical sheath that covers the stent prior to stent deployment by balloon expansion at the site of a dilated stenosis. Self-expanding stents are almost always contained within a cylindrical sheath which is pulled back to release the stent. If a sheath is not used, the rough surface of the stent can damage or remove endothelial cells from the arterial wall as the outer surface of the stent rubs the inside walls of the curved coronary (or other) arteries. Without a sheath, the stent may also get caught on the guiding catheter during movement into or out of the body which can cause the stent to come off the delivery catheter and embolize into the vasculature. When a sheath is used, it can have a few disadvantages. A first disadvantage is that all prior art sheaths are tubes that have a uniform wall thickness and are secured only at the proximal end to the stent delivery catheter system. Therefore, in order to have a sufficient column strength, the sheath must be relatively thick-walled, throughout its entire length, which makes it stiff and bulky so that passage through tortuous coronary arteries can be difficult. Another disadvantage of prior art sheaths is that they have blunt distal ends which can be caught on an already deployed stent, a calcified piece of intimal dissected tissue or a tight stenosis. Still further, when secured only at the proximal end of a stent delivery catheter, the sheath often either uncovers the stent due to significant bending of the stent delivery catheter or the sheath advances too far distally beyond the distal end of the stent. Finally, because of the larger diameter, blunt end and stiffness of sheathed stent delivery systems or the rough outer surface of unsheathed stent delivery systems, pre-dilatation with another balloon angioplasty catheter is almost always required before stent implantation.

Another disadvantage of existing stent delivery catheter systems that use either a conventional sheath or have stents mounted bare onto an inflatable balloon is that the distally directed push force for such stent delivery catheters comes only from the inner and outer shafts of the balloon angioplasty catheter on which the inflatable balloon is situated. Specifically, in no prior art device does the sheath contribute to the pushability of the stent delivery catheter system.

SUMMARY OF THE PRESENT INVENTION

The present invention is a stent delivery catheter system for placing a stent within a stenosis in a vessel of a human body. The stent delivery catheter system utilizes a slideable sheath with a thin-walled distal portion that is situated coaxially over a stent that is placed onto a balloon located at the distal portion of a balloon angioplasty catheter. The non-distal end of a central portion of the sheath has an interior shoulder which is capable of exerting a distally directed push force on the balloon angioplasty catheter at a point that is just proximal to the stent. This push force is then transferred through the non-deployed stent to a gradually tapered, highly flexible, lubricity coated distal tip of the balloon angioplasty catheter. The structure of a continuous outer surface extending backward from the distal tip and onto the distal section of the sheath, plus the lubricity coating of the outer surfaces of the distal tip and the sheath, plus the increased stent delivery catheter system pushability provided by the sheath and the stent itself makes it possible for the stent delivery catheter system to be pushed through even very tight stenoses. After the stent delivery catheter system is advanced over a guide wire so that the non-deployed stent is placed at the site of the stenoses, the sheath is then pulled back, the balloon is inflated and the stent is pushed radially outward resulting in dilatation of the stenosis. Thus the stent can be placed into even a tight stenosis without requiring pre-dilatation of that stenosis.

A preferred embodiment of the sheath uses a thin-walled metal tube for the sheath's proximal section which constitutes approximately 80% of the length of the sheath.

A central portion of the sheath is a comparatively thick-walled, flexible plastic tube or plastic plus wire tube whose distal end has an interior shoulder that engages a structure on the balloon angioplasty catheter at a point just proximal to the stent in order to exert a push force at that point onto a distal portion of the balloon angioplasty catheter. The distal portion of the sheath is a short (typically 2 to 5 cm long) tube that is very thin-walled and highly flexible. The purpose of using minimum wall thickness is to increase flexibility and decrease the outside diameter of the sheath in order to facilitate the pushing of the distal section of the stent delivery catheter system through a tight stenosis.

One embodiment of this invention has a proximal radiopaque marker band and a distal radiopaque marker band which are placed just proximal and just distal to the stent. Also, the stent can be advantageously placed between proximal and distal elastic tubes that go over the inflatable balloon and are situated just inside the radiopaque marker bands. The proximal elastic tube prevents the stent from being pulled backwards off the balloon when the sheath is pulled back prior to the stent deployment. Both radiopaque marker bands and both elastic tubes allow the push force exerted by the sheath to be transmitted to the catheter system's distal tip.

Another embodiment of this invention utilizes only proximal and distal elastic tubes that surround the stent but without any radiopaque marker bands. However, for this embodiment, the elastic tubes include a highly radiopaque metal powder within the elastomer of the elastic tube so as to enhance the tube's radiopacity to assist in placing the stent at the site of the stenosis.

Thus, an object of this invention is to have a stent delivery catheter system that has a sheath with an interior shoulder located at the distal end of a central portion of the sheath which interior shoulder can exert a distally directed push force at a point just proximal to a non-deployed stent mounted onto a balloon at a distal portion of a balloon angioplasty catheter.

Another object of this invention is to have a distal portion of the sheath which is a thin-walled plastic or plastic plus wire tube thus minimizing the outer diameter of the sheath and increasing flexibility.

Still another object of this invention is to utilize a non-deployed stent mounted onto a balloon at a distal portion of a balloon angioplasty catheter for transmitting a distally directed push force into a gradually tapered distal tip of a stent delivery catheter system.

Still another object of this invention is to utilize the proximal end of a radiopaque marker band placed proximal to the stent as a point at which an interior shoulder of a sheath exerts a distally directed push force into a distal portion of a balloon angioplasty catheter.

Still another object of this invention is to utilize the proximal end of a radiopaque elastic tube placed proximal to the stent as a point at which an interior shoulder of a sheath exerts a distally directed push force into a distal portion of a balloon angioplasty catheter.

Still another object of this invention is to utilize elastic tubes placed just proximal and just distal to the stent as a means to carry a distally directed push force into a gradually tapered distal tip of the stent delivery catheter system.

Still another object of this invention is to have a stent delivery catheter system that utilizes a gradually tapered, lubricity coated, elastomer, highly flexible tip in order to push a distal section of the stent delivery catheter system through a tight stenosis.

Still another object of this invention is to locate radiopaque marker bands and/or radiopaque elastic tubes placed just proximal and distal to a stent instead of placing such devices within an angioplasty balloon under the stent which placement within the balloon results in an increased outer diameter for the non-deployed stent.

Still another object of this invention is to use elastic tubes placed just proximal and distal to a stent to prevent the stent from being dislodged from its centered position on an inflatable balloon.

Still another object of this invention is to use elastic tubes placed just proximal and distal to a stent to prevent the stent from being dislodged from its post deployment position in the artery because the elastic tubes bring in the "wings" that would ordinarily form on the balloon after it is deflated, which "wings" could engage the deployed stent causing inadvertent stent displacement during removal of the balloon catheter.

Still another object of this invention is to have a stent delivery catheter system that can place a stent into a tight stenosis without first pre-dilating that tight stenosis.

Still another object of this invention is to utilize a slotted central section of the sheath through which the guide wire exits that allows a rapid exchange capability for the stent delivery catheter system.

These and other important objects and advantages of this invention will become apparent from the detailed description of the invention and the associated drawings provided herein.

BRIEF DESCRIPTION OF THE DRAWINGS

FIG. 2 shows a longitudinal cross section of the distal section of the stent delivery catheter system as it would be placed into an arterial stenosis prior to stent deployment.

FIG. 3 is a longitudinal cross section of the distal section of the stent delivery catheter system with the sheath pulled back thus uncovering the stent.

FIG. 4 shows a longitudinal cross section of the distal section of the stent delivery catheter system with the balloon inflated and the stent deployed outward so as to dilate the stenosis.

FIG. 5 is a longitudinal cross section of the dilated stenosis showing the stent deployed radially outward and the stent delivery catheter system removed from the patient's artery.

FIG. 7 is a longitudinal cross section of the stent delivery catheter system that illustrates a slotted sheath that allows a rapid exchange capability for the stent delivery catheter system.

FIG. 8 is a highly enlarged transverse cross section of the rapid exchange stent delivery catheter system at section 8—8 of FIG. 7.

FIG. 9 is a highly enlarged transverse cross section of the rapid exchange stent delivery catheter system at section 9—9 of FIG. 7.

FIG. 10 is a highly enlarged transverse cross section of the rapid exchange stent delivery catheter system at section 10—10 of FIG. 7.

DETAILED DESCRIPTION OF THE INVENTION

Figure 1:
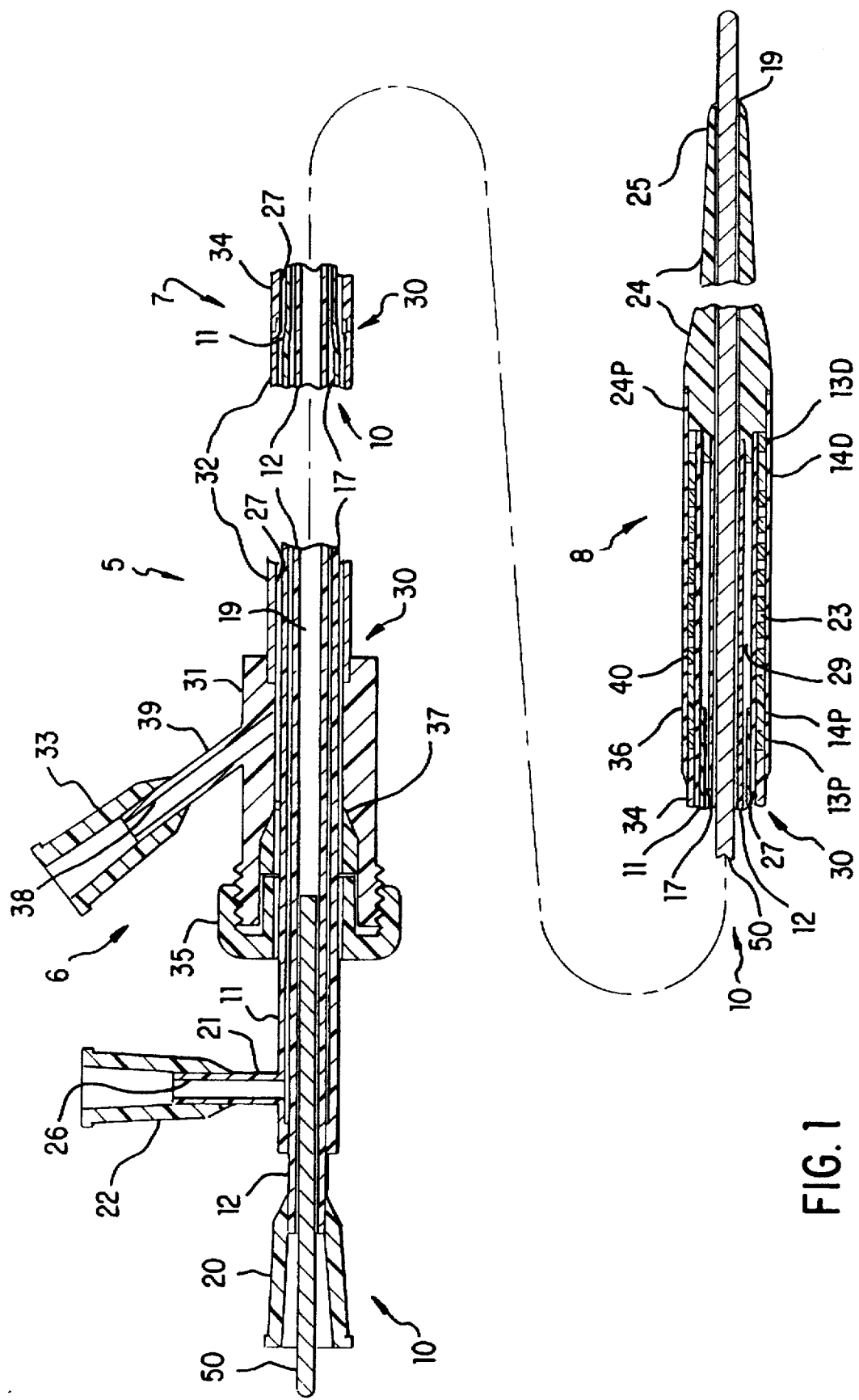
FIG. 1 is a longitudinal cross section of a stent delivery catheter system which illustrates the structure of the proximal, central and distal sections of the stent delivery catheter system.

FIG. 1 is a longitudinal cross section of a stent delivery catheter system 5 which is formed in three sections, namely; a proximal section 6, a center section 7 and a distal section 8. The stent delivery catheter system 5 consists of a balloon angioplasty catheter 10, a slideable sheath 30, a stent 40 and a guide wire 50.

The balloon angioplasty catheter 10 consists of an outer shaft 11, an inner shaft 12, a proximal radiopaque marker band 13P, a distal radiopaque marker band 13D, a proximal elastic band 14P, a distal elastic band 14D and a distal elastomer tip 24 having a thin-walled cylindrical end 25. At the proximal end of the balloon angioplasty catheter 10 is a Luer fitting 20 through which the guide wire 50 can be passed into the central lumen 19. Also at the proximal end of the balloon angioplasty catheter 10 is a side arm 21 having a Luer fitting 22 and a central passageway 26 that is in fluid communication with the annular passageway 17 that lies between the inner surface of the outer shaft 11 and the outer surface of the inner shaft 12. At the distal section 8 of the stent delivery catheter system 5, the balloon angioplasty catheter 10 has a distal portion which includes an angioplasty balloon 23 whose interior chamber 29 is in fluid communication with the annular passageway 17 and the central lumen 26 of the side arm 21. Thus, a source of inflation fluid can be inserted into or removed from the lumen 26 to inflate and deflate the balloon 23. Mounted on the balloon 23 is a balloon expandable stent 40 of any design that is well known in the art of balloon expandable stents.

The slideable sheath 30 is situated coaxially about the balloon angioplasty catheter 10. At the system's proximal section 6, the sheath 30 has a Tuohy-Borst fitting consisting of a main body 31 having a side arm 39 with a Luer fitting 33; the side arm 39 having a central lumen 38 that is in fluid communication with the annular passageway 27 that lies between the interior surface of the sheath 30 and the exterior surface of the outer shaft 11. The Tuohy-Borst fitting's main body 31 has a threaded proximal end onto which a nut 35 can be screwed on and off. Advancing the nut 35 compresses the elastomer gland 37 which causes a fluid seal to be made against the outer surface of the outer shaft 11. When such a fluid seal exists, no blood will leak from the Tuohy-Borst fitting and contrast liquid can be injected through the lumen 38 of the side arm 32 to flush air out of the annular passageway 27.

The sheath 30 has a thin-walled metal tube 32 for most of its length, which length is approximately 110 cm. As shown at the system's central section 7, the distal end of the tube 32 is joined to the proximal end of a flexible tube 34 whose distal end (located at the system's distal section 8) has an interior shoulder that is in contact with the proximal end of the proximal radiopaque marker band 13P. A thin-walled, highly flexible, tube 36 is fixedly attached at its proximal end to the distal end of the flexible tube 34. The distal end of the flexible tube 36 is configured to move slideably over a proximal section 24P of the tip 24. The metal tube 32 would typically be formed from stainless steel or Nitinol with a wall thickness between 0.01 and 0.1 mm. The outer diameter for the sheath 30 would typically be between 1.0 and 3.0 mm. The elastic tube 36 would typically have a wall thickness between 0.01 and 0.1 mm and would be made from any material typically used for catheters. Ideally the tube 36 would be formed from a plastic tube into which longitudinal metal wires are placed to prevent the tube from becoming wrinkled. Ideally these wires would be made from stainless steel or Nitinol.

The flexible tube 34 would typically have twice the wall thickness of the elastic tube 36. The construction of the tube 34 would typically be a composite of a metal wire with a plastic material typically used for intravascular catheters.

The operation of the stent delivery catheter system 5 is best explained with the assistance of FIGS. 2, 3, 4 and 5.

FIG. 2 shows the distal section 8 already advanced over the guide wire 50 until the non-deployed stent 40 is centered within an arterial stenosis 2 located within an artery 1. The radiopaque marker bands 13P and 13D are used by the doctor implanting the stent 23 to center the stent 23 in the stenosis 2. It should be understood that the very gradually tapered shape of the tip 24 and the continuous outer surface of the tip 24 and the outer surface of the cylinder 36, each of which can have a lubricious outer coating, facilitates penetration through even a tight arterial stenosis. The tip 24 can be made radiopaque by forming it from a compound of a dense metal such as tungsten into an elastomer such as polyurethane.

FIG. 3 shows the sheath 30 pulled back so that the stent 40 is ready to be expanded. Pull back of the sheath 30 is accomplished by holding the Luer fitting 20 at the proximal portion of the stent delivery catheter 10 fixed while pulling back on the nut 35 of the Tuohy-Borst fitting at the proximal portion of sheath 30. This is accomplished after the nut 35 is somewhat loosened so that the gland 37 slides easily over the outer shaft 11.

FIG. 4 shows an inflated balloon 23' that causes the stent 40' to dilate the stenosis 2'. It should be noted that the elastomer tubes 14P' and 14D' become distorted when the balloon 23' is inflated. After the balloon 23' is deflated, the tubes 14P' and 14D' revert to their original shape as shown for the tubes 14P and 14D in FIGS. 1, 2 and 3.

FIG. 5 shows the stent 40' in place with the balloon angioplasty catheter 10, sheath 30 and guide wire 50 removed from the patient's arterial system. Although the stent delivery catheter system 5 is most valuable for stenting of stenoses in coronary arteries, it should be understood that it can be used in any vessel of the human body. It should also be noted that the system 5 can be readily used in tight arterial stenoses without requiring pre-dilatation by means of a separate, very low profile balloon angioplasty catheter. This capability for stent insertion without pre-dilatation saves both time and cost when placing stents into an arterial stenosis. It should also be noted that the elastic tubes 14P and 14D exactly center the stent 40 on the balloon 23. Also, the tube 14P prevents the stent 40 from moving in the proximal direction when the sheath 30 is pulled back. Still further it should be noted that this invention can be used with either balloon expandable or self-expanding stents, and the balloon angioplasty catheter can be of either the "over-the-wire" design or of a "rapid-exchange" design.

The most important capability of the stent delivery catheter system 5 is its ability to be pushed through even a very tight stenosis. This capability originates from several specific aspects of the design of the catheter system 5, namely, the small outside diameter of the tube 36 because of its thin wall, the extraordinarily gradual taper of the lubricity coated distal tip 24, the continuous outer surface from the tip 24 onto the tube 36, and the very high, distally directed push force achieved by means of the sheath 30 acting through the non-deployed stent 40. A "gradually tapered" distal tip 24 is obtained when the average slope of the tip relative to the longitudinal axis of the central lumen 19 at the distal portion of the balloon angioplasty catheter 10 is less than 3 degrees and never more than 10 degrees. Optimally, an average slope for the tip 24 would be determined from a maximum radius of 0.6 mm at the tip's proximal end to a radius of 0.22 mm at the tips distal end. With a tip length of 15 mm, this gives an average slope for the tip 24 of 0.6−0.22/15=0.025 which is a slope angle of approximately 1.5 degrees relative to the longitudinal axis of the central lumen 17 of the distal portion of the balloon angioplasty catheter 10. Such a gradual taper greatly enhances the capability of the stent delivery catheter system 5 to penetrate through a tight stenosis.

The system 5 obtains its capability to push the distal tip 24 through a tight stenosis by a series of structures each of which is capable of significant pushability. This series of structures that provide excellent pushability for the stent delivery catheter system 5 are as follows:

(1) The Tuohy-Borst fitting at the proximal end of the sheath 30 which fitting lies outside the patient's body.

(2) The thin-walled, typically stainless steel tube 32 that extends for most of the length of the stent delivery catheter system 5.

(3) The comparatively thick-walled, flexible tube 34 that is typically a composite cylinder made from wire and an elastomeric plastic.

(4) The proximal radiopaque marker band 13P whose outside diameter is greater than the inner diameter of the interior shoulder located at the distal end of the flexible tube 34. Therefore, the distal end of the tube 34 can effectively apply a distally directed push force onto the proximal end of the rigid, cylindrical radiopaque marker band 13P thus continuing the pushability of the sheath 30. It is at the intersection of the interior shoulder at the distal end of the tube 34 with the proximal end of the proximal radiopaque marker band 13P that the sheath pushability is transferred from the sheath to a distal portion of the balloon angioplasty catheter 10.

(5) The push force is next carried forward in the distal direction by the proximal elastic tube 14P which is adjacent to the proximal radiopaque marker band 13P and also adjacent to a proximal section of the balloon 23.

(6) The stent 23 is the next structure that transmits the distally directed push force to the distal tip 24.

(7) The distal elastic tube 14D which is attached to a distal portion of the balloon 23 transmits the push force to the distal radiopaque marker band 13D.

(8) The distal radiopaque marker band 13D, which can be molded into the distal tip 24, is the last link in the pushability chain that enhances the capability of the stent delivery catheter system 5 to push the distal tip 24 through a tight stenosis.

In summary, the pushability of the sheath 30 as transferred to a distal portion of the balloon angioplasty catheter 10 is very much greater than the pushability of the outer shaft 11 and inner shaft 12 by themselves. It should be noted that the design of the stent delivery catheter system 5 allows the sheath's distal tube 36 to be both very thin-walled and highly flexible, and no contribution to pushability is required of that structure.

The thin-walled, flexible design of the tube 36 provides improved capability of the system 5 to place the stent 23 into a tight arterial stenosis because its flexibility improves passage through the tortuous vasculature of coronary arteries, and not requiring pushability from the tube 36 because of its thin wall, minimizes the outside diameter of the system 5 thus again improving the system's capability for placing the stent 23 into a tight stenosis.

Figure 6:
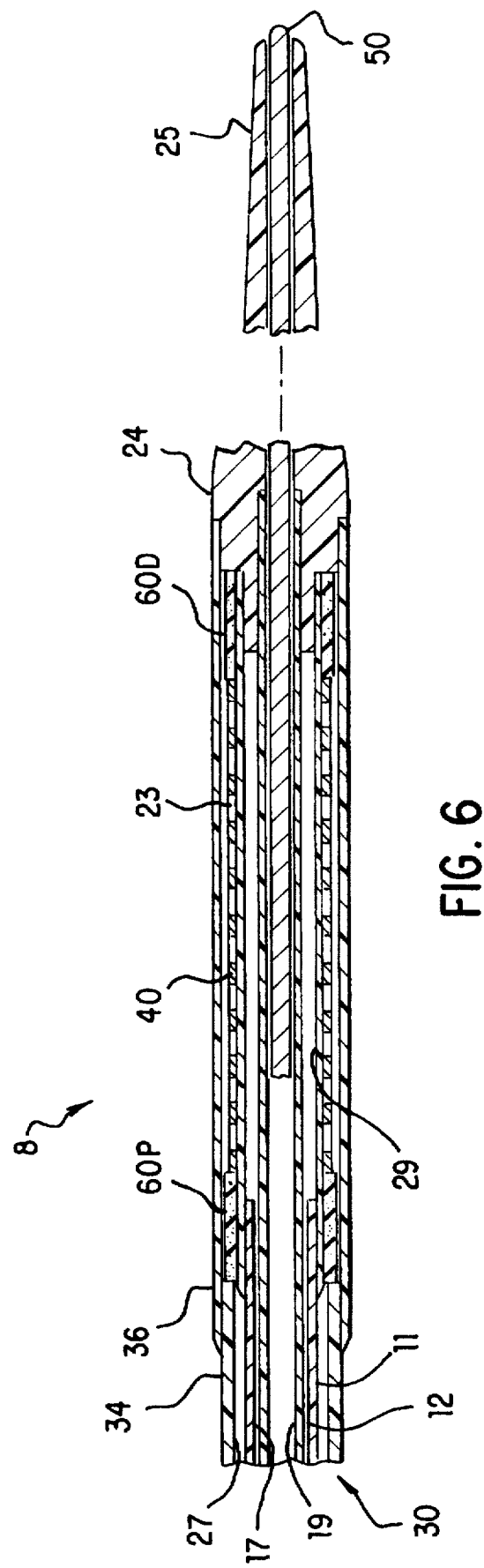
FIG. 6 is longitudinal cross section of the distal section of a stent delivery catheter system using radiopaque elastic tubes placed just proximal and distal to the stent.

FIG. 6 is another embodiment of the distal section 8 of a stent delivery catheter system. The only difference between the embodiment of FIG. 6 compared with FIG. 1 is that in FIG. 6 the proximal and distal radiopaque marker bands 13P and 13D have been eliminated and the elastic bands 14P and 14D have been replaced with the proximal elastic band 60P and the distal elastic band 60D. The bands 60P and 60D would typically be longer than the bands 14P and 14D, and furthermore, the bands 60P and 60D would contain some material to make them radiopaque. Typically, powdered tungsten or tantalum could be placed into an elastomer such as silicone rubber or polyurethane to make the bands 60P and 60D both elastic and radiopaque.

FIGS. 7, 8, 9 and 10 illustrate a stent delivery catheter system 70 which is a "rapid-exchange" design; i.e., the proximal exit of the guide wire 50 lies just proximal to the proximal end of the stent 40 as opposed to an "over-the-wire" design as shown in FIG. 1 where the guide wire 50 exits at the proximal end of the system 5. FIGS. 7 to 10 inclusive show the elastic radiopaque marker band 60P, the balloon 23, the stent 40, annular passageways 17 and 27 all of which elements are of the same design as shown for FIG. 1. The new aspects of the design shown in FIGS. 7 to 10 inclusive include a slotted sheath 61 having a narrow elongated slot or keyway 62 into which the key 67 is placed. The proximal portion of the rapid-exchange balloon angioplasty catheter is a dual lumen tube 63 that has a balloon access lumen 64 through which fluid can be injected or removed to inflate or deflate the balloon 23. A distal portion of the guide wire lumen 65 is used for inserting the guide wire 50 through a port 66. A very thin-walled short metal joining tube 73 is used to sealingly join the guide wire lumen 65 to the inner shaft 72. The outer shaft 71 is sealingly joined at its proximal end to the distal end of the dual-lumen tube 63. The entire structure of the system 70 that is distal to the metal joining tube 73 is identical in construction to the distal portion 8 of FIG. 6 except for the slot 62 in the sheath 61.

It should be noted that the slot 62 and key 67 cooperate to prevent the distal section of the sheath 61 from rotating about the dual-lumen tube 63. The length of the slot 62 is sufficient to allow the thin-walled tube 36 to be pulled back far enough to completely uncover the stent 40.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A stent delivery catheter system for placing a stent within a stenosis of a vessel in a human body, the system comprising:

a flexible guide wire;

a balloon angioplasty catheter having a distal portion and having an inflatable balloon which has a proximal end and a distal end, the balloon being located at the distal portion of the balloon angioplasty catheter and a stent coaxially mounted around the balloon; the balloon angioplasty catheter also having a flexible, gradually tapered, distal tip which has a central lumen through which the guide wire can be slideably moved; and a sheath generally in the form of an elongated cylinder that is coaxially located around the balloon angioplasty catheter, the sheath having a central portion and a distal portion, the sheath being adapted to apply a push force to the distal portion of the balloon angioplasty catheter at a point proximal to the stent which push force is transmitted through the distal portion of the balloon angioplasty catheter which enables the distal tip to be pushed through the stenosis in the vessel of the human body.

2. The system of claim 1 wherein the distal portion of the sheath includes a thin-walled, highly flexible tube which lies coaxilly around the stent and the central portion of the sheath has a proximal end and a distal end, the highly flexible tube having a proximal section that is fixedly attached to the distal end of the central portion of the sheath, the central portion also having an interior shoulder at its distal end which shoulder is situated inside the flexible tube, the shoulder at the distal end of the central potion of the sheath being adapted to provide a distally directed push force onto the distal portion of the balloon angioplasty catheter.

3. The system of claim 2 wherein the highly flexible tube at the distal portion of the sheath is formed from a plastic material into which metal wires are inserted.

4. The system of claim 3 wherein the metal of the metal wires is Nitinol.

5. The system of claim 1 wherein the sheath has three cylindrical tube portions; a first portion being a proximal portion of the sheath and being in the form of a thin-walled metal tube which has a distal end, the sheath also having a second portion which is the central portion that has a proximal end and a distal end, the central portion being joined at its proximal end to the distal end of the proximal portion of the sheath and the central portion being joined at its distal end to a third portion of the sheath which is the distal portion which distal portion is a thin-walled, highly flexible tube, the wall thickness of the central portion being greater than the wall thickness of either the proximal portion or distal portion of the sheath, and the distal end of the central portion of the sheath being adapted to exert a distally directed push force onto the distal portion of the balloon angioplasty catheter.

6. The system of claim 5 wherein the metal tube forming the proximal portion of the sheath is made from stainless steel.

7. The system of claim 5 wherein the metal tube forming, the proximal portion of the sheath is made from Nitinol.

8. The system of claim 1 wherein the balloon angioplasty catheter includes a proximal radiopaque marker band located proximal to the stent and a distal radiopaque marker band that lies distal to the stent, both radiopaque marker bands being located at the distal portion of the balloon angioplasty catheter.

9. The system of claim 8 wherein the push force from the sheath is exerted against the proximal radiopaque marker band.

10. The system of claim 8 wherein the stent is centrally located between the proximal radiopaque marker band and the distal radiopaque marker band.

11. The system of claim 1 wherein there is a proximal elastic band located just proximal to the stent and a distal elastic band located just distal to the stent, the distally directed push force from the sheath being exerted through both the proximal and distal elastic bands, the elastic bands being formed from an elastomeric plastic.

12. The system of claim 11 wherein the proximal and distal elastic bands include a radiopaque component that is placed within the elastomeric plastic of the elastic band.

13. The system of claim 1 wherein the average slope of the gradually tapered distal tip relative to a longitudinal axis of the central lumen of the distal portion of the balloon angioplasty catheter is less than 3 degrees.

14. The system of claim 1 wherein the average slope of the gradually tapered distal tip relative to a longitudinal axis of the central lumen of the distal portion of the balloon angioplasty catheter is less than approximately 1.5 degrees.

15. The system of claim 1 wherein a narrow elongated slot is located in the side of the sheath which slot serves as a proximal exit port for the guide wire thus providing the stent delivery catheter system with rapid exchange capability.

* * * * *